US012700123B2

(12) United States Patent
Iwane

(10) Patent No.: US 12,700,123 B2
(45) Date of Patent: Aug. 4, 2026

(54) ENDOSCOPE SYSTEM AND METHOD OF OPERATING THE SAME

(71) Applicant: FUJIFILM Corporation, Tokyo (JP)

(72) Inventor: Kosuke Iwane, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 361 days.

(21) Appl. No.: 18/463,897

(22) Filed: Sep. 8, 2023

(65) Prior Publication Data

US 2023/0419535 A1 Dec. 28, 2023

Related U.S. Application Data

(63) Continuation of application No. PCT/JP2022/009715, filed on Mar. 7, 2022.

(30) Foreign Application Priority Data

Mar. 9, 2021 (JP) ................................. 2021-037557

(51) Int. Cl.
*G06T 7/70* (2017.01)
*A61B 1/00* (2006.01)
(52) U.S. Cl.
CPC .............. *G06T 7/70* (2017.01); *A61B 1/0005* (2013.01); *G06T 2207/10068* (2013.01); *G06T 2207/30096* (2013.01)
(58) Field of Classification Search
CPC .............. G06T 7/70; G06T 2207/10068; G06T 2207/30096; G06T 7/00; A61B 1/0005; A61B 1/000096; A61B 1/0638; A61B 1/0655; A61B 1/000094; A61B 1/045
USPC ....................................................... 382/103
See application file for complete search history.

(56) References Cited

U.S. PATENT DOCUMENTS

| | | | |
|---|---|---|---|
| 11,759,092 B2 | 9/2023 | Oosake et al. | |
| 2014/0031659 A1 | 1/2014 | Zhao et al. | |
| 2015/0078615 A1* | 3/2015 | Staples, II | ................ G06T 7/50 382/103 |
| 2019/0015163 A1* | 1/2019 | Abhari | ................... H04N 7/181 |
| 2020/0008653 A1 | 1/2020 | Kamon | |

(Continued)

FOREIGN PATENT DOCUMENTS

| | | |
|---|---|---|
| CN | 105473098 A | 4/2016 |
| CN | 110461210 A | 11/2019 |

(Continued)

OTHER PUBLICATIONS

International Search Report issued in PCT/JP2022/009715; mailed May 17, 2022.

(Continued)

*Primary Examiner* — Jennifer Mehmood
*Assistant Examiner* — Pardis Sohraby
(74) *Attorney, Agent, or Firm* — Studebaker Brackett PLLC

(57) ABSTRACT

In a case where the detection target is detected, an actual position display control process of displaying a detected position display circle on a display in an actual position display mode (single line) is performed. In a case where the detection target is not detected, an estimated position display control process of displaying an estimated position display circle on the display in an estimated position display mode (double line) different from the actual position display mode is performed.

13 Claims, 13 Drawing Sheets

(56) References Cited

U.S. PATENT DOCUMENTS

| | | | |
|---|---|---|---|
| 2020/0090333 A1 | | 3/2020 | Iwaki |
| 2020/0297422 A1* | | 9/2020 | Gocho ............... A61B 1/00055 |
| 2020/0345225 A1 | | 11/2020 | Iwane |
| 2021/0000327 A1 | | 1/2021 | Kitamura et al. |
| 2021/0106208 A1 | | 4/2021 | Iwaki |
| 2021/0158520 A1* | | 5/2021 | Kamon ................. G06T 7/0012 |
| 2021/0287395 A1 | | 9/2021 | Ishikake et al. |
| 2022/0051397 A1 | | 2/2022 | Takahashi et al. |
| 2022/0087568 A1 | | 3/2022 | Allenby et al. |
| 2022/0148182 A1 | | 5/2022 | Kiyuna et al. |
| 2022/0254017 A1 | | 8/2022 | Rivlin et al. |
| 2023/0414064 A1 | | 12/2023 | Kubo |
| 2023/0421887 A1 | | 12/2023 | Iwane |

FOREIGN PATENT DOCUMENTS

| | | | |
|---|---|---|---|
| CN | 111683583 A | 9/2020 | |
| CN | 116963654 A | 10/2023 | |
| CN | 116963655 A | 10/2023 | |
| JP | 2011-036371 A | 2/2011 | |
| JP | 2015-529489 A | 10/2015 | |
| WO | 2018/159461 A1 | 9/2018 | |
| WO | 2018/216188 A1 | 11/2018 | |
| WO | 2019/106712 A1 | 6/2019 | |
| WO | 2019/146066 A1 | 8/2019 | |
| WO | 2019/202827 A1 | 10/2019 | |
| WO | 2019/244255 A1 | 12/2019 | |
| WO | 2020/040087 A1 | 2/2020 | |
| WO | 2020/054604 A1 | 3/2020 | |
| WO | 2020/110278 A1 | 6/2020 | |
| WO | 2020/183936 A1 | 9/2020 | |
| WO | 2020/242949 A1 | 12/2020 | |

OTHER PUBLICATIONS

International Preliminary Report on Patentability (Chapter I) and Written Opinion of the International Searching Authority issued in PCT/JP2022/009715; issued Sep. 12, 2023.

Extended European Search Report issued in EP 22 76 7085.8-1122 by the European Patent Office on Oct. 2, 2024, which is related to U.S. Appl. No. 18/463,897.

The partial supplementary European search report (R. 164 EPC) issued by the European Patent Office on Jul. 11, 2024, which corresponds to European Patent Application No. 22767085.8-1122 and is related to U.S. Appl. No. 18/463,897.

"Notice of Reasons for Refusal" Office Action issued in JP 2023-505543; mailed by the Japanese Patent Office on Feb. 3, 2026.

An Office Action; mailed by the China National Intellectual Property Administration of the People's Republic of China on Apr. 2, 2026, which corresponds to Chinese Patent Application No. 202280020353.0 and is related to U.S. Appl. No. 18/463,897.

* cited by examiner

FIG. 2

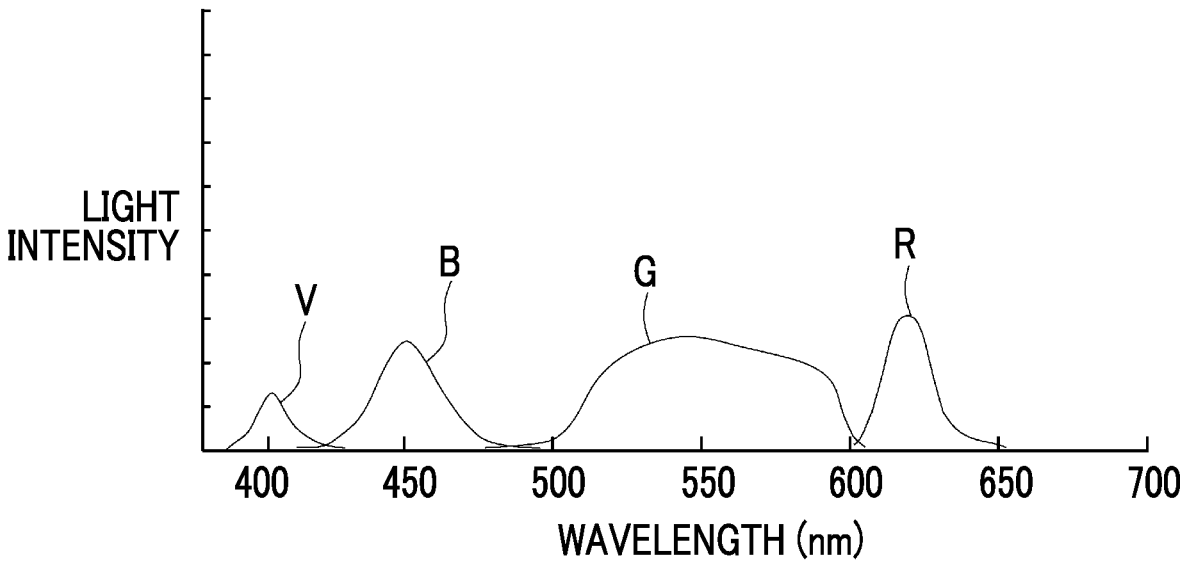

FIG. 3A

| ONE FRAME | ONE FRAME | ONE FRAME | ONE FRAME | ONE FRAME | ONE FRAME |
|---|---|---|---|---|---|
| ILLUMINATION LIGHT L | ILLUMINATION LIGHT L | ILLUMINATION LIGHT L | ILLUMINATION LIGHT L | ILLUMINATION LIGHT L | ILLUMINATION LIGHT L |

FIG. 3B

| ONE FRAME | ONE FRAME | ONE FRAME | ONE FRAME | ONE FRAME | ONE FRAME |
|---|---|---|---|---|---|
| FIRST ILLUMINATION LIGHT L1 | FIRST ILLUMINATION LIGHT L1 | SECOND ILLUMINATION LIGHT L2 | FIRST ILLUMINATION LIGHT L1 | FIRST ILLUMINATION LIGHT L1 | SECOND ILLUMINATION LIGHT L2 |

FIG. 8
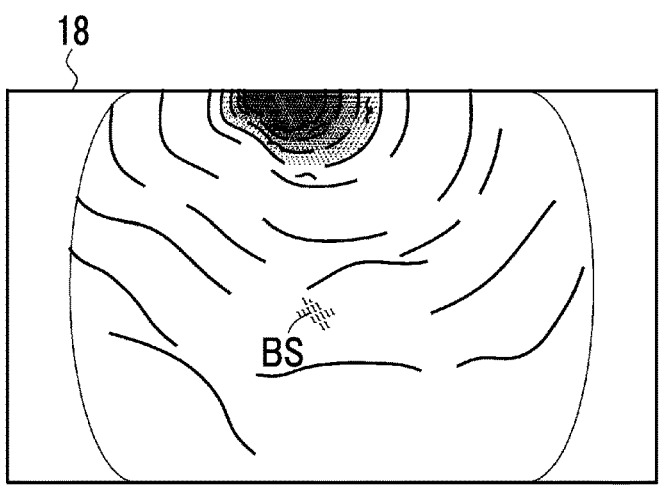
ACTUAL POSITION DISPLAY
CONTROL PROCESS
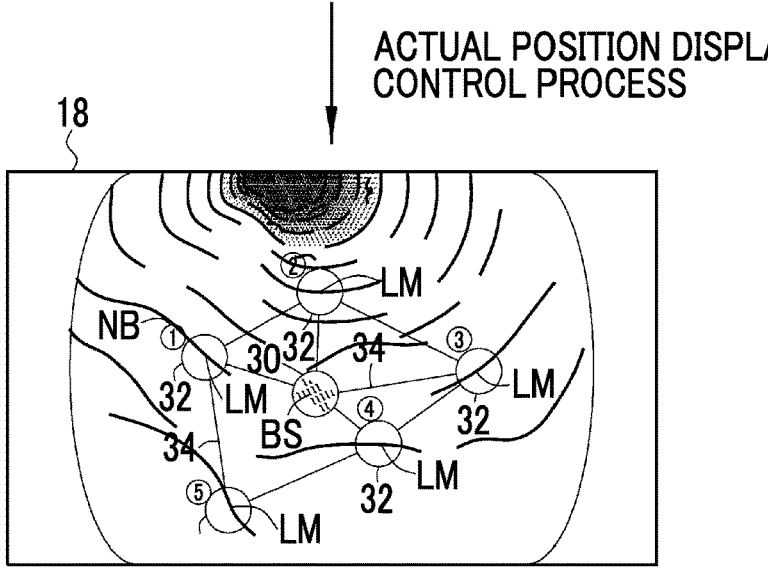
LANDMARK DISPLAY
CONTROL PROCESS
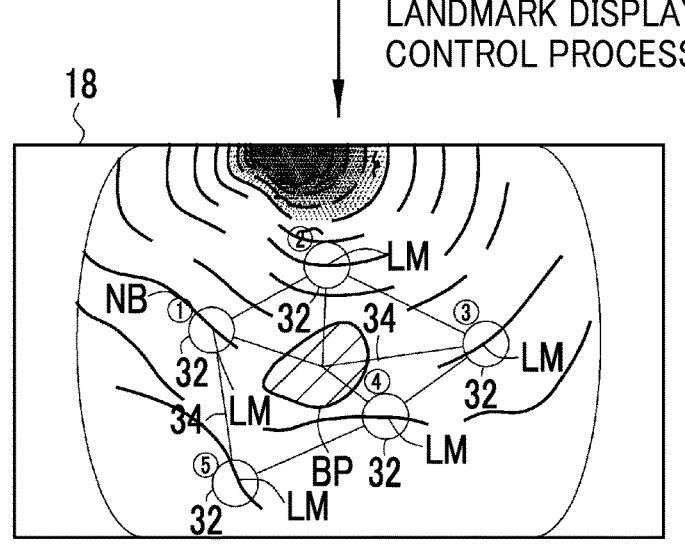

FIG. 9
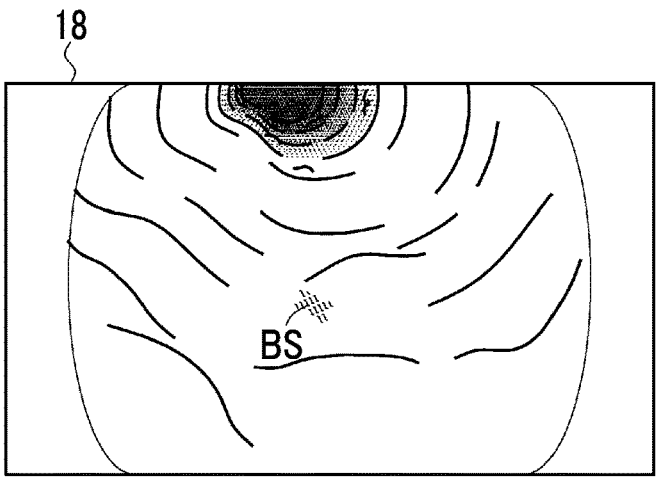
ACTUAL POSITION DISPLAY
CONTROL PROCESS
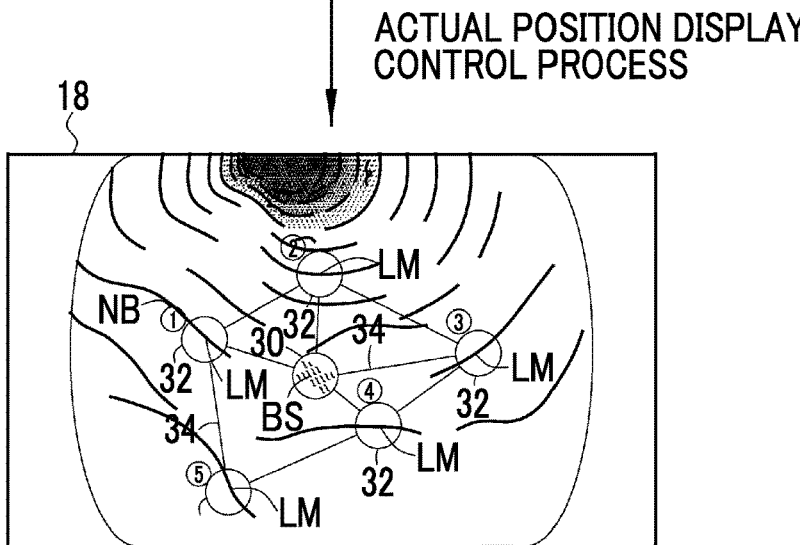
ESTIMATED POSITION DISPLAY
CONTROL PROCESS
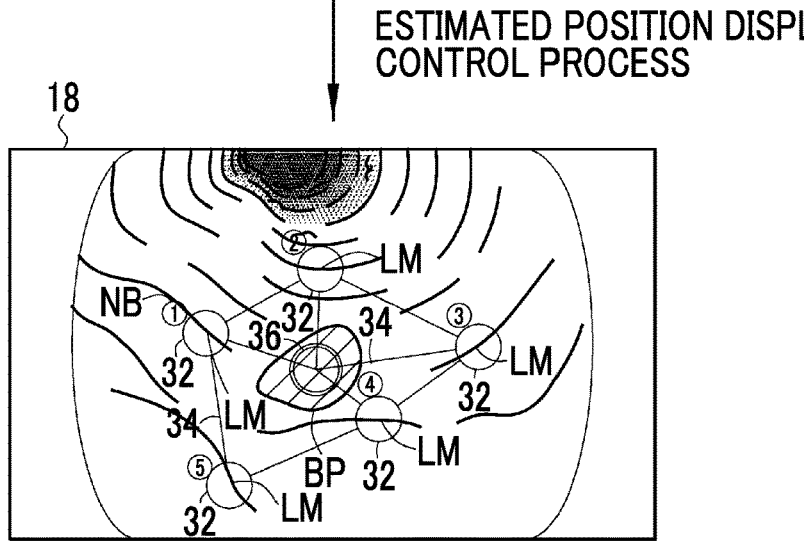

FIG. 10

| | ACTUAL POSITION DISPLAY MODE | ESTIMATED POSITION DISPLAY MODE |
|---|---|---|
| POSITION DISPLAY COLOR INFORMATION | BLUE | GREEN |
| POSITION DISPLAY FIGURE | CIRCLE OR ELLIPSE (ACTUAL POSITION LINE TYPE) | CIRCLE OR ELLIPSE (ESTIMATED POSITION LINE TYPE) |
| | CIRCLE OR ELLIPSE (ACTUAL POSITION LINE THICKNESS) | POLYGON (ESTIMATED POSITION LINE THICKNESS) |
| | CIRCLE OR ELLIPSE (ACTUAL POSITION SIZE) | CIRCLE OR ELLIPSE (ESTIMATED POSITION SIZE) |
| | CIRCLE OR ELLIPSE | POLYGON |
| | POLYGON | CIRCLE OR ELLIPSE |

FIG. 11
(A)
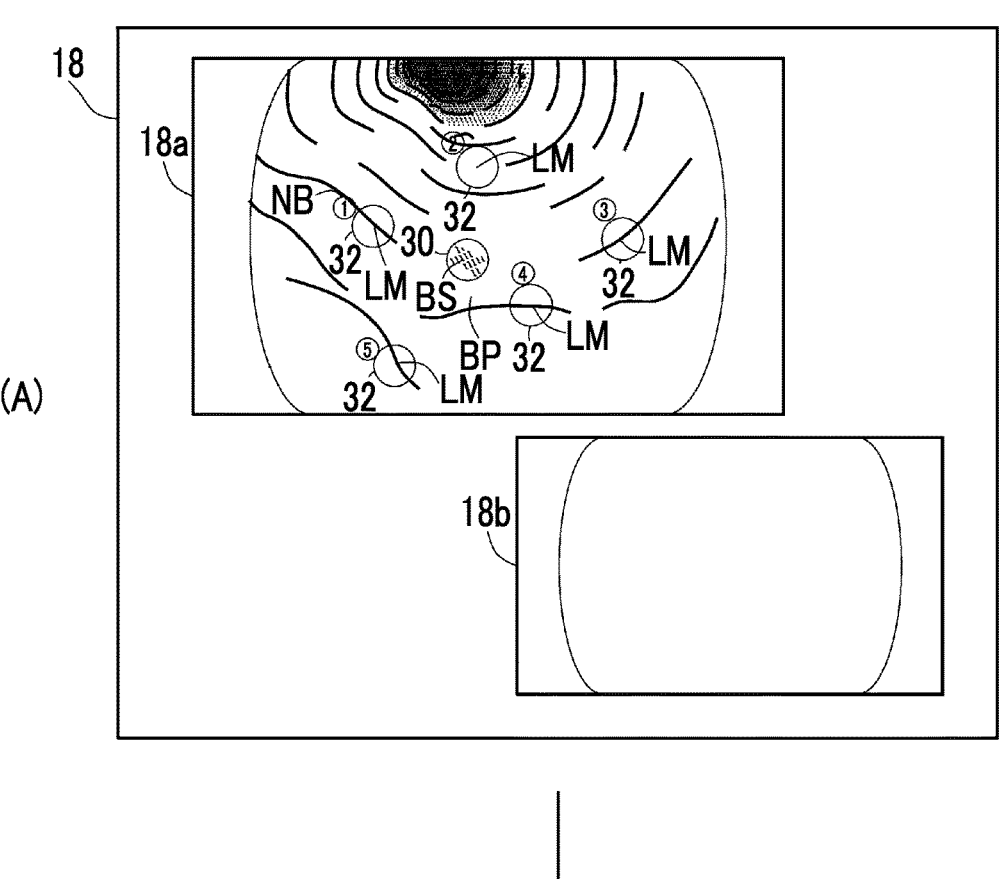
(B)
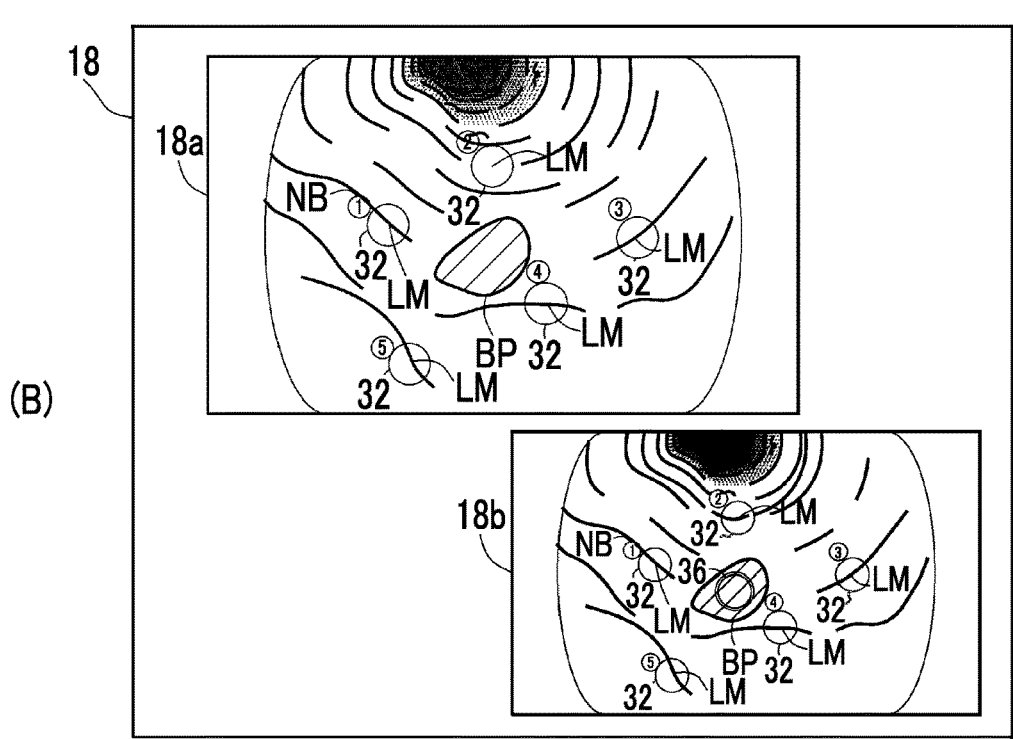

FIG. 13
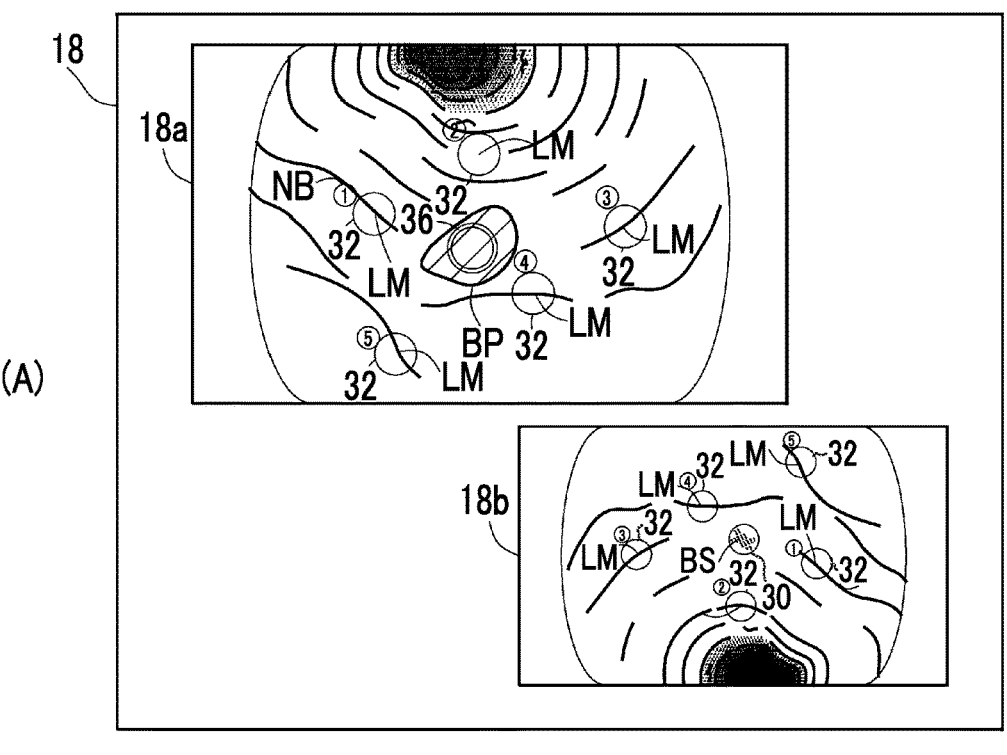
(A)
IMAGE ROTATION
OF SUB SCREEN
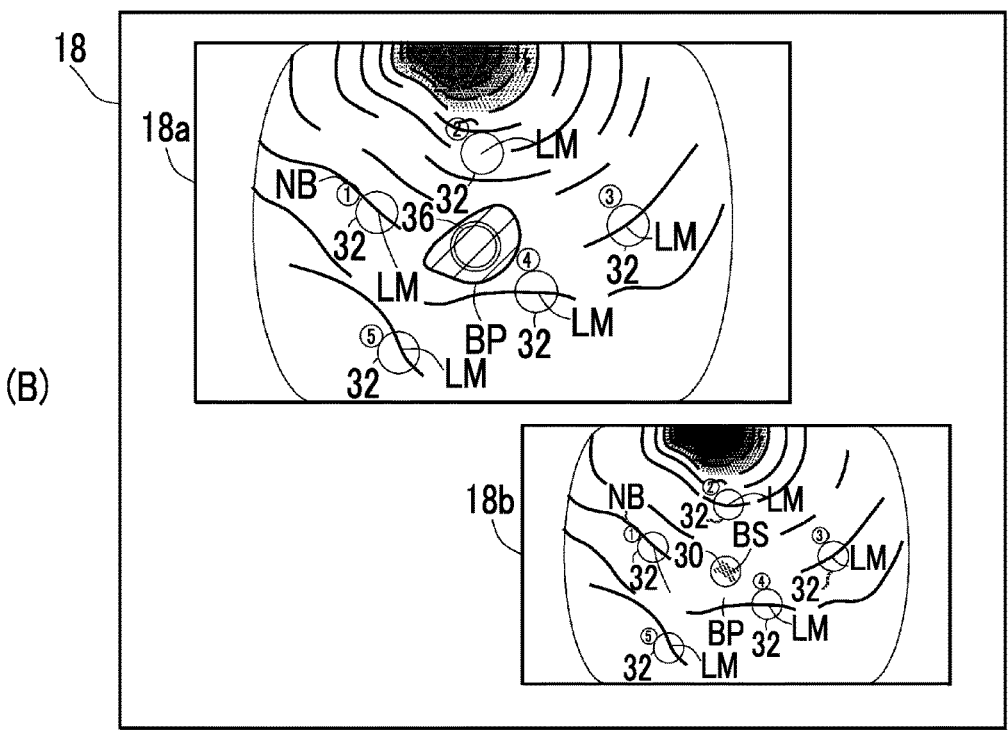
(B)

FIG. 14

|  | HIGH RELIABILITY DEGREE | LOW RELIABILITY DEGREE |
|---|---|---|
| POSITION DISPLAY COLOR INFORMATION | HIGH DENSITY | LOW DENSITY |
| POSITION DISPLAY FIGURE | FIGURE SIZE IS SMALL | FIGURE SIZE IS LARGE |
|  | LINE THICKNESS IS THICK | LINE THICKNESS IS THIN |
|  | LINE TYPE IS SOLID | LINE TYPE IS DOTTED |

FIG. 15

|  | DETECTION TARGET DETECTION PROCESS | POSITION INFORMATION ESTIMATION PROCESS |
|---|---|---|
| START TIMING | AT TIME OF WATER SUPPLY DETECTION<br>AT TIME OF INCISION DETECTION<br>AT TIME OF TREATMENT TOOL USE DETECTION | AT TIME OF FAILURE OF POSITION INFORMATION ESTIMATION PROCESS |
| END TIMING | AT TIME OF FAILURE OF DETECTION TARGET DETECTION PROCESS<br>AFTER ELAPSE OF PREDETERMINED TIME AFTER FAILURE | AT TIME OF FAILURE OF POSITION INFORMATION ESTIMATION PROCESS (AT TIME OF LANDMARK DISAPPEARANCE) |

(A)

NEW LANDMARK IS DETECTED
NEW LANDMARK SETTING PROCESS (B)

A PART OF LANDMARKS
IS NOT DETECTED (C)

ENDOSCOPE SYSTEM AND METHOD OF OPERATING THE SAME

CROSS-REFERENCE TO RELATED APPLICATIONS

This application is a Continuation of PCT International Application No. PCT/JP2022/009715 filed on 7 Mar. 2022, which claims priority under 35 U.S.C § 119(a) to Japanese Patent Application No. 2021-037557 filed on 9 Mar. 2021. The above application is hereby expressly incorporated by reference, in its entirety, into the present application.

BACKGROUND OF THE INVENTION

1. Field of the Invention

The present invention relates to an endoscope system that detects a detection target, such as a bleeding portion, and a method of operating the same.

2. Description of the Related Art

In a medical field, an endoscope system including a light source device, an endoscope, and a processor device has been widely used. In endoscopic diagnosis, there is a case where a detection target such as a bleeding portion is detected during endoscopic treatment. The detection of the detection target has been performed not only by detection by visual observation but also estimation by comparison with a past image. WO2019/202827A1, JP2015-529489A (corresponding to US2014/031659A1), and JP2011-036371A disclose that a bleeding portion or region is detected from an image.

SUMMARY OF THE INVENTION

However, it is difficult to specify a position of the detection target by visual observation or from an image in a case where a factor that reduces visibility of the detection target, such as accumulated blood due to bleeding, occurs over time.

An object of the present invention is to provide an endoscope system and a method of operating the same with which a position of a detection target can be specified even in a case where the visibility of the detection target is reduced.

An endoscope system according to an aspect of the present invention comprises: a processor, in which the processor is configured to: acquire an endoscope image; detect a detection target and acquire actual position information of the detection target by performing a detection target detection process on the endoscope image; calculate estimated position information of the detection target by a position information estimation process based on the endoscope image in a case where the detection target is not detected; and perform any of an actual position display control process of displaying the actual position information of the detection target on a display in an actual position display mode in a case where the detection target is detected, or an estimated position display control process of displaying the estimated position information of the detection target on the display in an estimated position display mode different from the actual position display mode in a case where the detection target is not detected.

It is preferable that in a case where position display color information is used for displaying the actual position information and the estimated position information of the detection target, the position display color information of the actual position display mode is different from the position display color information of the estimated position display mode, or, in a case where a position display figure is used for displaying the actual position information and the estimated position information of the detection target, the position display figure of the actual position display mode is different from the position display figure of the estimated position display mode.

It is preferable that in a case where the position display figure is a circle or an ellipse, at least any of a case where an actual position line type and an estimated position line type are different from each other, a case where an actual position line thickness and an estimated position line thickness are different from each other, or a case where an actual position size and an estimated position size are different from each other is true. It is preferable that a shape of the position display figure of the actual position display mode is different from a shape of the position display figure of the estimated position display mode.

It is preferable that in a case where the display has a main screen on which the endoscope image is displayed and a sub screen provided at a position different from a position of the main screen, the estimated position information of the detection target is displayed on the sub screen as the estimated position display mode. It is preferable that in a case where the display has a main screen on which the endoscope image is displayed and a sub screen provided at a position different from a position of the main screen, the estimated position information of the detection target is displayed on the main screen in the estimated position display mode and the actual position information of the detection target is displayed on the sub screen in the actual position display mode by the estimated position display control process.

It is preferable that in the estimated position display control process, the estimated position display mode is changed according to a reliability degree of the estimated position information. It is preferable that in the position information estimation process, the estimated position information is calculated from a detection target region including the detection target. It is preferable that the processor is configured to set at least any of a start timing or an end timing of the detection target detection process, or a start timing or an end timing of the position information estimation process. It is preferable that the detection target is at least any of a bleeding portion, a lesion part, a shape of a specific organ, a mucous membrane pattern, marking after cauterization, or marking given to a body.

An endoscope system according to the aspect of the present invention comprises: a processor, in which the processor is configured to: acquire an endoscope image; acquire detection target actual position information of a detection target by performing a first detection process on the endoscope image; acquire position information of a landmark by performing a second detection process on the endoscope image; perform a landmark setting process of setting a relative relationship by associating any of the detection target actual position information or detection target estimated position information obtained from a position information estimation process based on the position information of the landmark, with the position information of the landmark each time the endoscope image is updated and the detection target actual position information or the detection target estimated position information is acquired; and display the detection target actual position information or the detection target estimated position information on a display.

It is preferable that in a case where a new landmark is detected by acquiring the endoscope image of a new frame in a state where the position information estimation process is continued, a new landmark setting process of setting a new relative relationship by associating the detection target estimated position information with the new landmark is performed as the landmark setting process, after the new landmark setting process, in a case where the landmark necessary for the position information estimation process is not recognized, a position information estimation process based on the new relative relationship is performed, and a new detection target estimated position information is calculated, and the new detection target estimated position information is displayed on the display. It is preferable that the new landmark is position information of at least any of a mucous membrane pattern, a shape of an organ, or marking by a user operation.

A method of operating an endoscope system according to the aspect of the present invention comprises: via a processor, a step of acquiring an endoscope image; a step of detecting a detection target and acquiring actual position information of the detection target by performing a detection target detection process on the endoscope image; a step of calculating estimated position information of the detection target by a position information estimation process based on the endoscope image in a case where the detection target is not detected; and a step of performing any of an actual position display control process of displaying the actual position information of the detection target on a display in an actual position display mode in a case where the detection target is detected, or an estimated position display control process of displaying the estimated position information of the detection target on the display in an estimated position display mode different from the actual position display mode in a case where the detection target is not detected.

According to the present invention, it is possible to specify the position of the detection target even in a case where the visibility of the detection target is reduced.

BRIEF DESCRIPTION OF THE DRAWINGS

FIG. 2 is a graph showing spectra of violet light V, blue light B, green light G, and red light R.

FIG. 3A is an explanatory diagram showing a mono-light emission mode, and FIG. 3B is an explanatory diagram showing a multi-light emission mode.

FIG. 8 is an explanatory diagram showing an actual position display control process and a landmark display control process.

FIG. 9 is an explanatory diagram showing an actual position display control process and an estimated position display control process.

FIG. 10 is an explanatory diagram showing an actual position display mode and an estimated position display mode.

(A) of FIG. 11 is an image diagram showing an actual position display mode, and (B) of FIG. 11 is an image diagram showing an estimated position display mode in which estimated position information is displayed on a sub screen.

Figure 12:
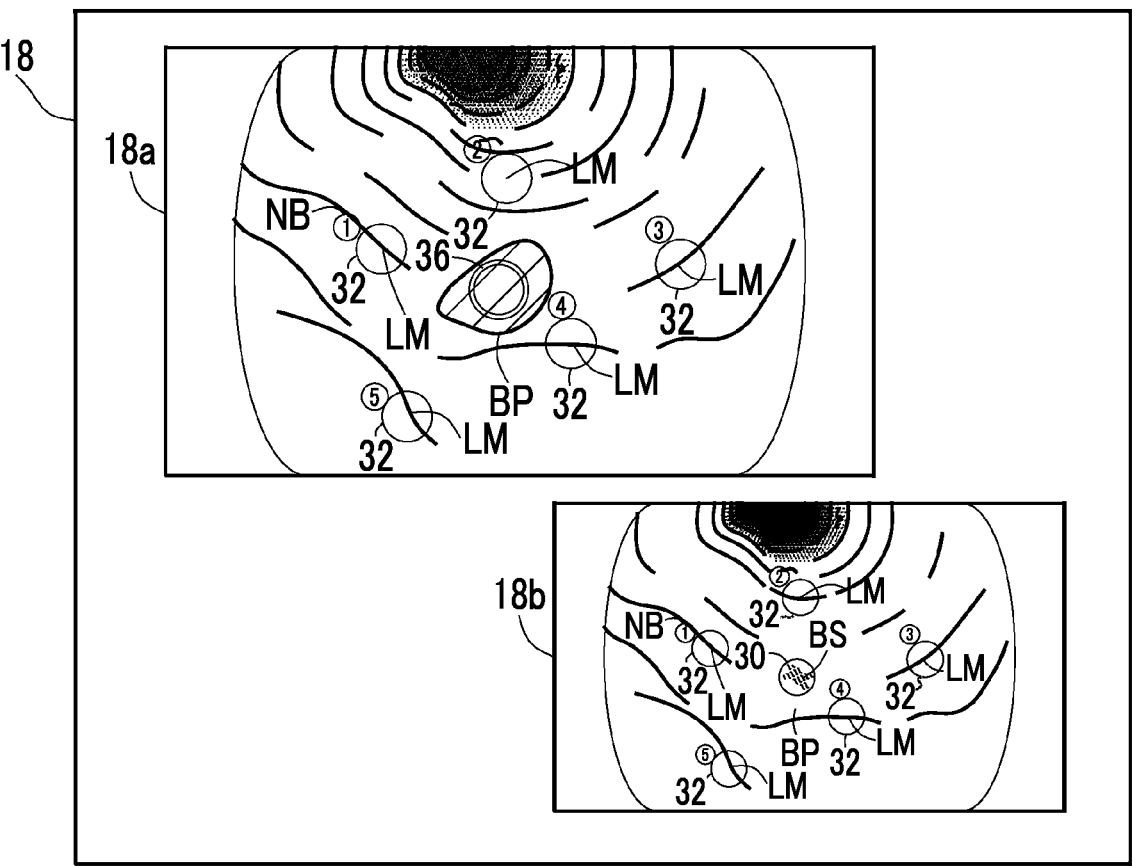

FIG. 12 is an image diagram showing an estimated position display mode in which estimated position information is displayed on a main screen.

FIG. 13 is an explanatory diagram showing that an image of the sub screen is rotated by 180 degrees.

FIG. 14 is an explanatory diagram showing an estimated position display mode that changes according to a reliability degree of the estimated position information.

FIG. 15 is an explanatory diagram showing a start timing and an end timing of a detection target detection process and a position information estimation process.

Figure 16:
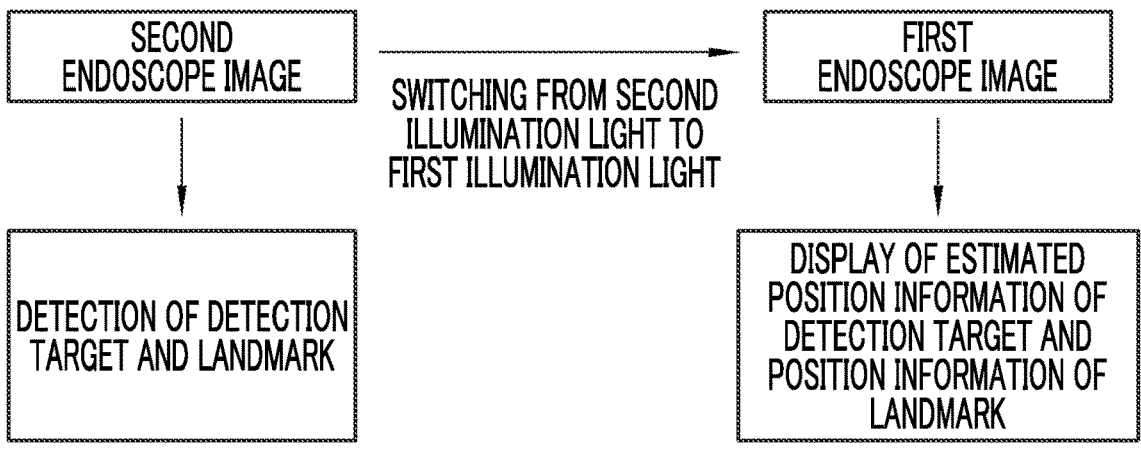

FIG. 16 is an explanatory diagram showing that a detection target and a landmark are detected from a second endoscope image, and that actual position information of the detection target and position information of the landmark are displayed from a first endoscope image.

Figure 17:
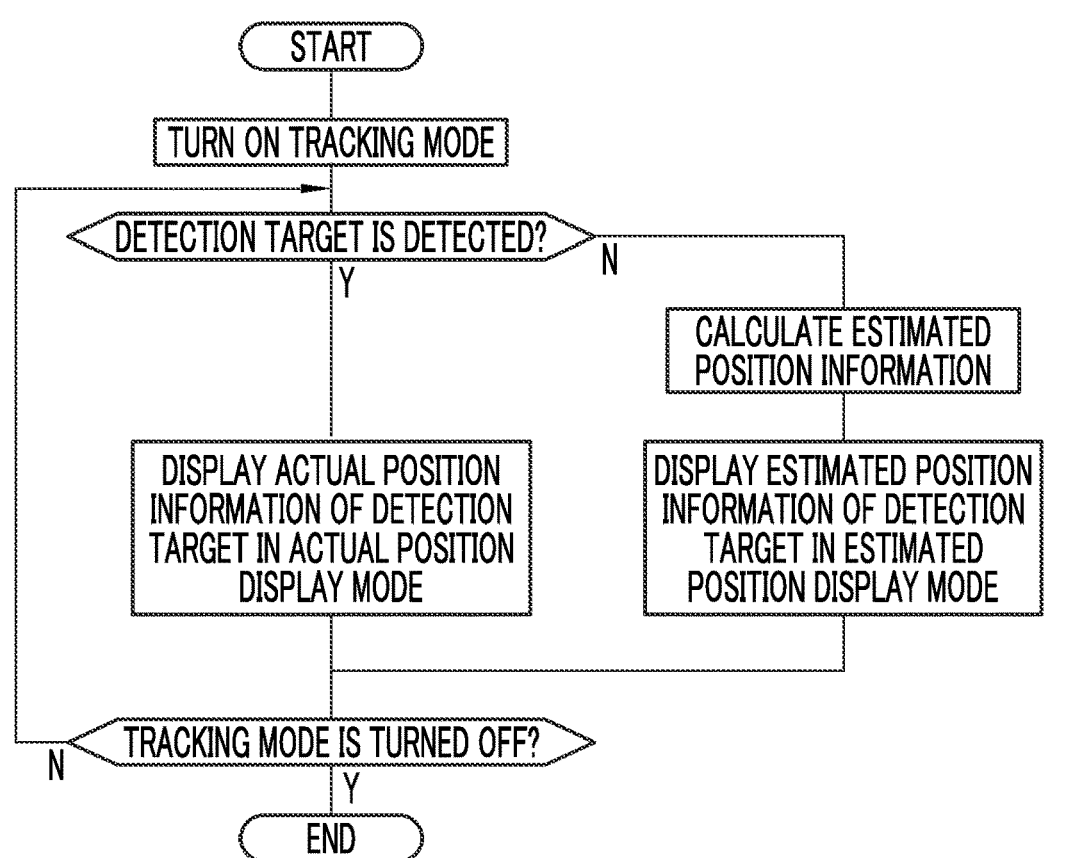

FIG. 17 is an explanatory diagram showing a series of flows in a tracking mode.

Figure 18:
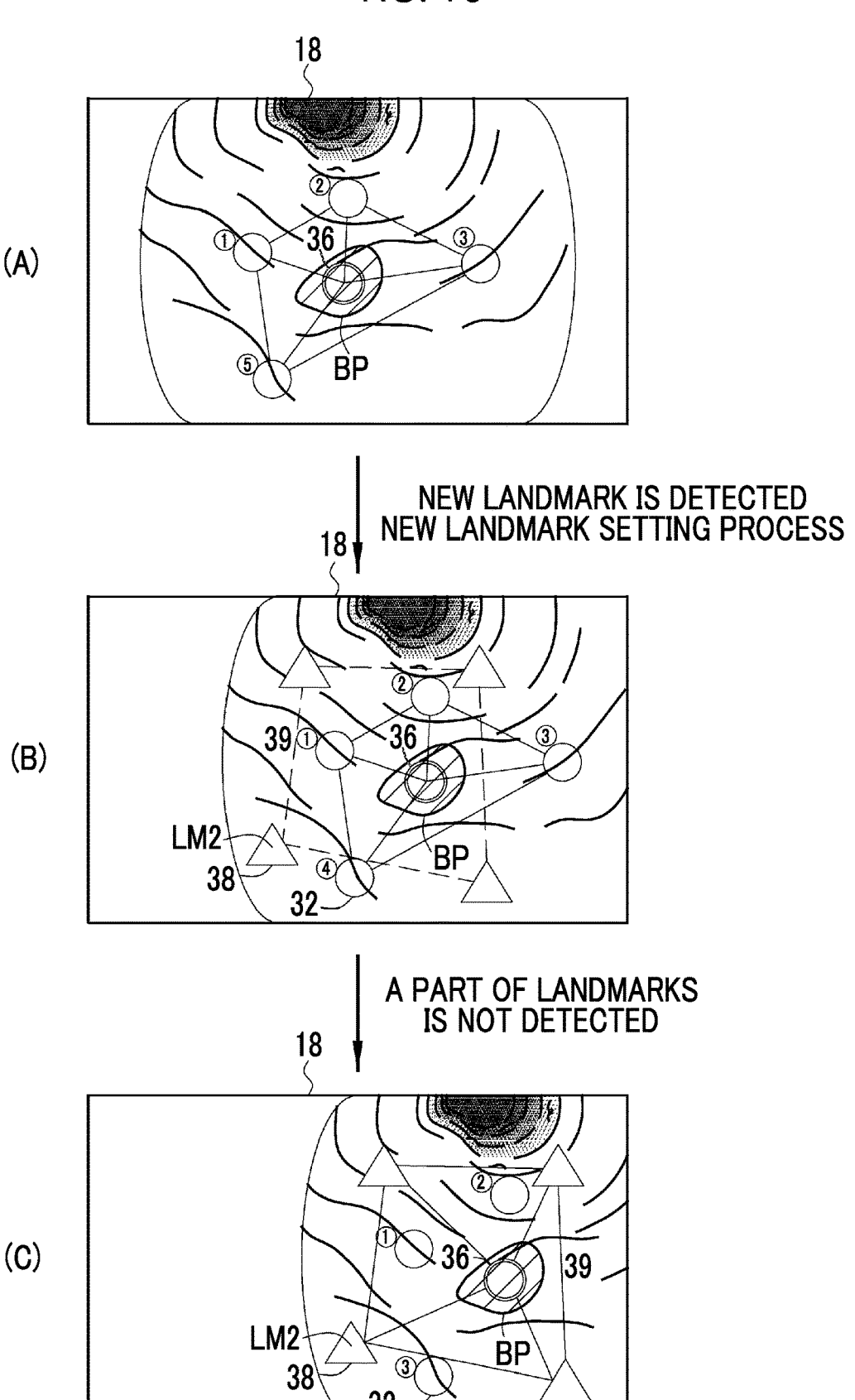

FIG. 18 is an explanatory diagram showing an update of a landmark used in a position information estimation process.

DESCRIPTION OF THE PREFERRED EMBODIMENTS

Figure 1:
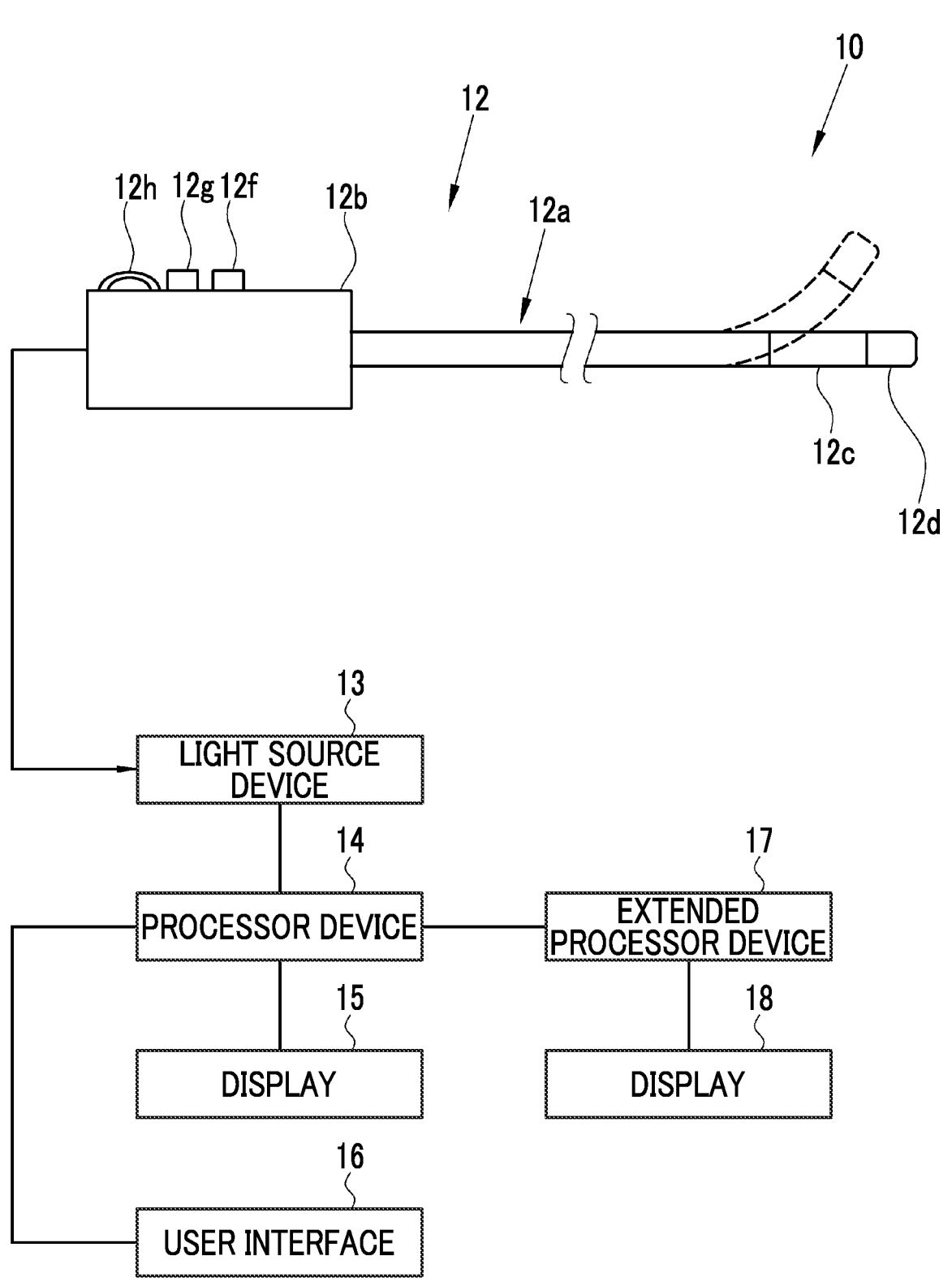
FIG. 1 is a schematic view of an endoscope system.

As shown in FIG. 1, an endoscope system 10 includes an endoscope 12, a light source device 13, a processor device 14, a display 15, a user interface 16, an extended processor device 17, and a display 18. The endoscope 12 is optically connected to the light source device 13 and is electrically connected to the processor device 14. The light source device 13 supplies illumination light to the endoscope 12.

The endoscope 12 is used for illuminating an observation target with illumination light and imaging the observation target to acquire an endoscope image. The endoscope 12 includes an insertion part 12a to be inserted into a body of the observation target, an operating part 12b provided at a base end portion of the insertion part 12a, and a bendable part 12c and a distal end part 12d provided on a distal end side of the insertion part 12a. The bendable part 12c performs a bending operation by operating the operating part 12b. The distal end part 12d irradiates the observation target with illumination light and receives reflected light from the observation target to image the observation target. The distal end part 12d is directed in a desired direction by the bending operation of the bendable part 12c. The operating part 12b includes a mode selector switch 12f used for a mode switching operation, a still image acquisition instruction switch 12g used for providing an instruction of acquisition of a still image of the observation target, and a zoom operation part 12h used for an operation of a zoom lens 21b.

The processor device 14 is electrically connected to the display 15 and the user interface 16. The processor device 14 receives the endoscope image from the endoscope 12. The display 15 outputs and displays an image, information, or the like of the observation target processed by the processor device 14. The user interface 16 includes a keyboard, a mouse, a touch pad, a microphone, and the like, and has a function of receiving an input operation such as function setting. The extended processor device 17 is electrically connected to the processor device 14. The extended processor device 17 receives the image or various kinds of information from the processor device 14. The display 18 outputs and displays an image, information, or the like processed by the extended processor device 17.

The endoscope system 10 comprises a mono-light emission mode and a multi-light emission mode, and the modes are switched by the mode selector switch 12f. The mono-light emission mode is a mode in which the observation target is continuously illuminated with illumination light having the same spectrum. The multi-light emission mode is a mode in which the observation target is illuminated while switching a plurality of illumination light beams having different spectra according to a specific pattern. The illumination light includes normal light (broadband light such as white light) used for giving brightness to the entire observation target to observe the entire observation target, or special light used for emphasizing a specific region of the observation target. Further, in the mono-light emission mode, the illumination light may be switched to illumination light having a different spectrum by the operation of the mode selector switch 12f. For example, first illumination light and second illumination light having different spectra may be switched.

The mono-light emission mode and the multi-light emission mode include a tracking mode, and the tracking mode can also be switched by the mode selector switch 12f. The tracking mode is a mode in which actual position information of a detection target is detected, and position information of the detection target and position information of a landmark associated with the position information of the detection target are displayed on the display 18 (or the display 15) in order to allow a user to grasp a position of the detection target such as a bleeding portion even though a change occurs in an image of a subject or the like.

As shown in FIG. 2, the illumination light is preferably emitted by a combination of violet light V, blue light B, green light G, and red light R. The violet light V preferably has a central wavelength of 405±10 nm and a wavelength range of 380 to 420 nm. The blue light B preferably has a central wavelength of 450±10 nm and a wavelength range of 420 to 500 nm. The green light G preferably has a wavelength range of 480 to 600 nm. The red light R preferably has a central wavelength of 620 to 630 nm and a wavelength range of 600 to 650 nm.

The light source device 13 independently controls the light amounts of the four colors of violet light V, blue light B, green light G, and red light R. As shown in FIG. 3A, in the case of the mono-light emission mode, illumination light L having the same spectrum is continuously emitted for each frame. On the other hand, in the case of the multi-light emission mode, control is performed to change the light amounts of the four colors of violet light V, blue light B, green light G, and red light R in accordance with a specific pattern. For example, as shown in FIG. 3B, as the specific pattern, there is a pattern in which a first light emission pattern in which first illumination light L1 having a first spectrum is emitted for two consecutive frames and a second light emission pattern in which second illumination light L2 having a second spectrum different from the first spectrum is emitted for one frame are alternately performed. The frame refers to a time from when an imaging sensor (not shown) provided in the distal end part 12d of the endoscope starts receiving reflected light from the observation target to when output of charge signals accumulated based on the light reception is completed.

Figure 4:
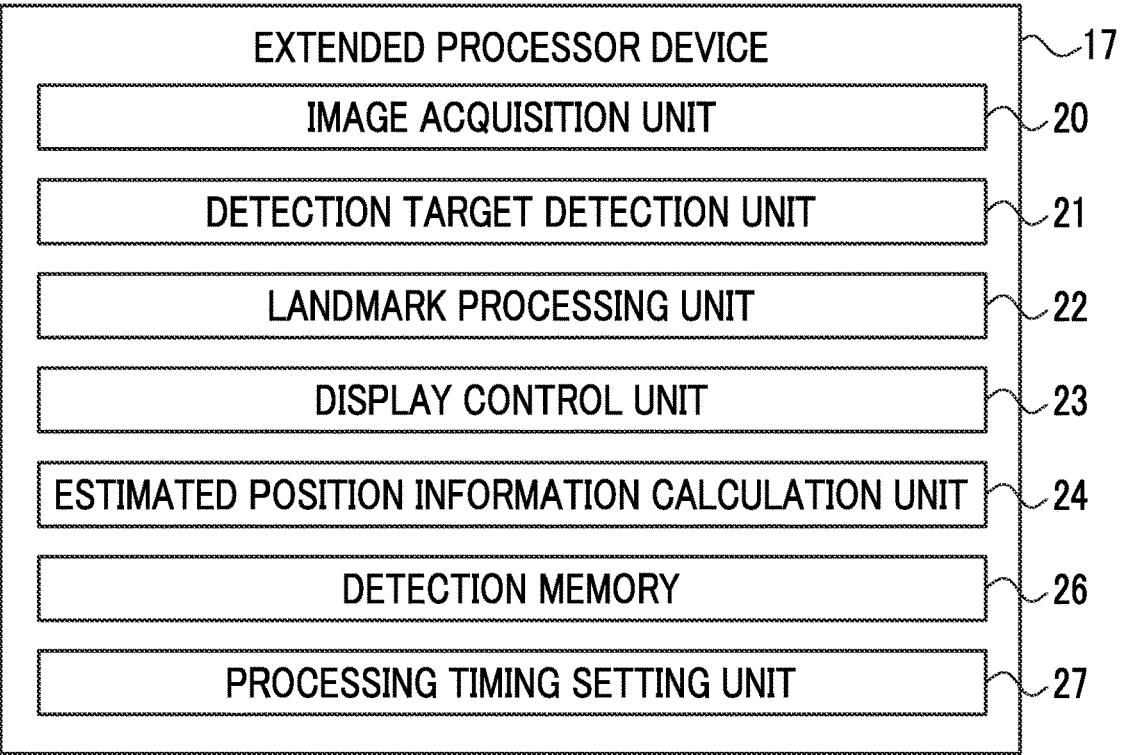
FIG. 4 is a block diagram showing functions of an extended processor device.

As shown in FIG. 4, the extended processor device 17 comprises an image acquisition unit 20, a detection target detection unit 21, a landmark processing unit 22, a display control unit 23, an estimated position information calculation unit 24, a detection memory 26, and a processing timing setting unit 27. The extended processor device 17 is provided with a program memory that stores programs related to various kinds of processing. The program is executed by a processor provided in the extended processor device 17 to implement functions of the image acquisition unit 20, the detection target detection unit 21, the landmark processing unit 22, the estimated position information calculation unit 24, the display control unit 23, and the processing timing setting unit 27. The display control unit 23 may perform display control of the display 15 in addition to display control of the display 18.

The image acquisition unit 20 acquires the endoscope image transmitted from the processor device 14. The processor device 14 transmits the endoscope image to the extended processor device 17 for each frame. The image acquisition unit acquires the endoscope image for each frame transmitted from the processor device 14.

Figure 5:
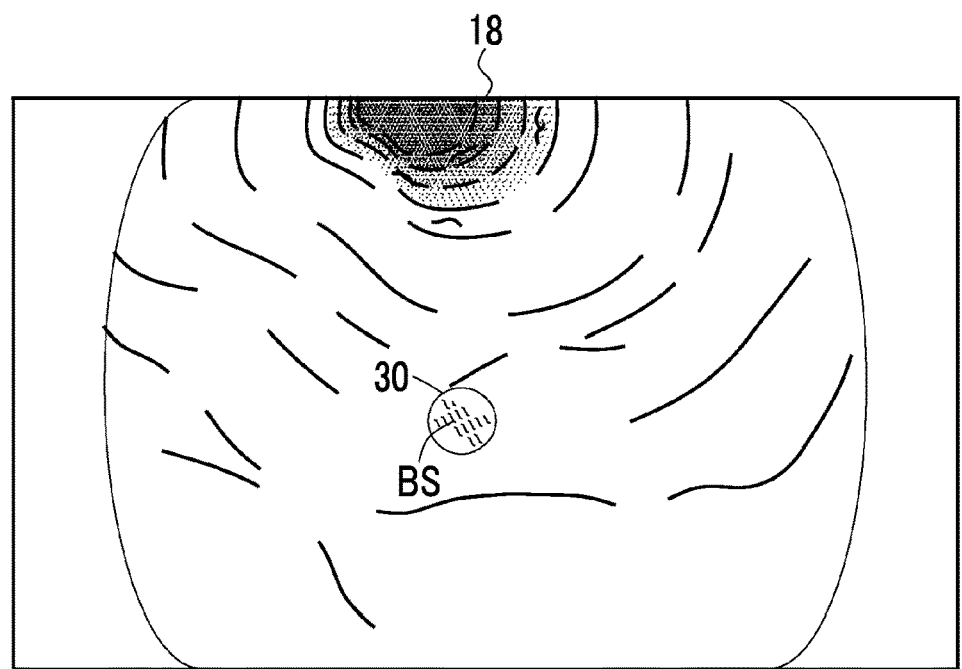
FIG. 5 is an image diagram showing a bleeding portion detected by a detection target detection process and a detected position display circle.

The detection target detection unit 21 detects a detection target and acquires actual position information of the detection target by performing a detection target detection process on the endoscope image. As shown in FIG. 5, in a case where a bleeding portion BS, which is one of the detection targets, is detected in the endoscope image of the display 18 by the detection target detection process, the display control unit 23 displays a detected position display circle 30 around the bleeding portion BS on the display 18 as actual position information of the bleeding portion BS. The detection target is preferably at least one of a bleeding portion BS, a lesion part such as cancer, a lesion part emphasized by chemical fluorescence (photodynamic diagnosis (PDD)), a shape of a specific organ, a mucous membrane pattern, marking after cauterization, or marking given to a body (marking given by a coloring agent or marking with lame or marker given on a bulging agent to be injected in a case of incision). In addition, a lesion part (for example, a hypoxic part) emphasized by chemical fluorescence may be weakly emphasized over time and may be difficult to be visually recognized. Therefore, in such a case, it is possible to grasp the lesion part by estimating a surrounding landmark or the like.

It is preferable that the detection target detection unit 21 is a trained model that has been trained through machine learning using teacher image data including the detection target. The machine learning includes supervised learning, semi-unsupervised learning, unsupervised learning, reinforcement learning, deep reinforcement learning, learning using a neural network, deep learning, and the like. In a case where the detection target is detected by the detection target detection process, information on the detected detection target is stored in the detection memory 26.

Figure 6:
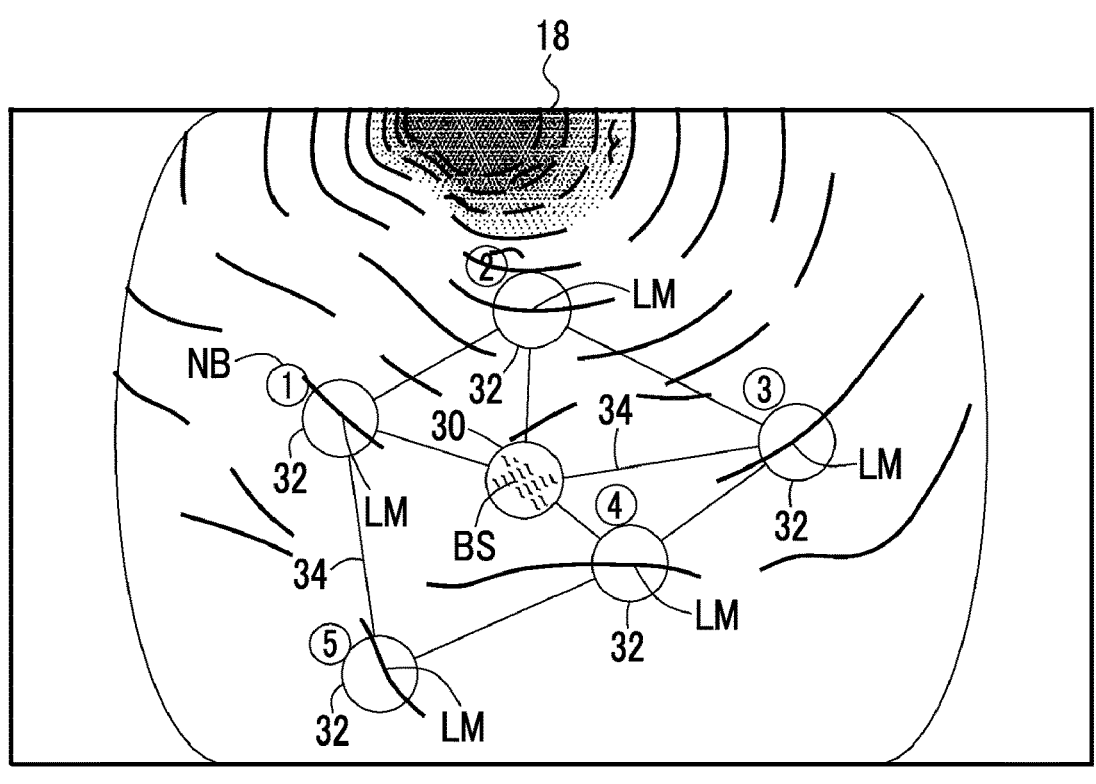
FIG. 6 is an image diagram showing a detected position display circle, a landmark detected by a landmark detection process, and a landmark position display circle.

In a case where the detection target is detected by the detection target detection unit 21, the landmark processing unit 22 detects a landmark and acquires position information of the landmark by performing a landmark detection process on the endoscope image. Examples of the landmark include various structures such as blood vessels and glandular structures. As shown in FIG. 6, in a case where a plurality of landmarks LM are detected by the landmark detection process in the endoscope image in which the bleeding portion BS, which is one of the detection targets, is detected, the display control unit 23 displays a plurality of landmark position display circles 32 on the display 18 as position information of the landmarks LM. In this case, it is preferable that the landmark position display circles 32 can be distinguished from each other. For example, a number NB (distinction number) for distinction is assigned to each of the landmark position display circles 32. The landmark LM is preferably detected not only in the vicinity of the detection target such as a bleeding region, but also from a position away from the detection target in order to eliminate a factor that reduces the visibility of the detection target, such as accumulated blood flowing out from the bleeding portion.

In a case where the landmark is detected by the landmark detection process, a landmark setting process of associating the position information of the landmark with the actual position information of the detection target is performed. As shown in FIG. 6, in the landmark setting process, as a method of associating the position information of the landmark LM with the actual position information of the detection target, the detected position display circle 30 and the landmark position display circle 32 are connected with a link line 34. In this case, it is preferable to associate the position information of the landmark LM detected around the detection target among the landmarks LM with the actual position information of the detection target. That is, in the case of FIG. 6, the landmark position display circles 32 having the distinction numbers "1", "2", "3", "4", and "5" around the detected position display circle 30 need to be connected to at least the detected position display circle 30 with the link line 34. In addition, it is preferable to connect the landmark position display circles 32 to each other with the link line 34. Information relating to the position information of the landmark LM and the actual position information of the detection target associated by the landmark setting process is stored in the detection memory 26.

Figure 7:
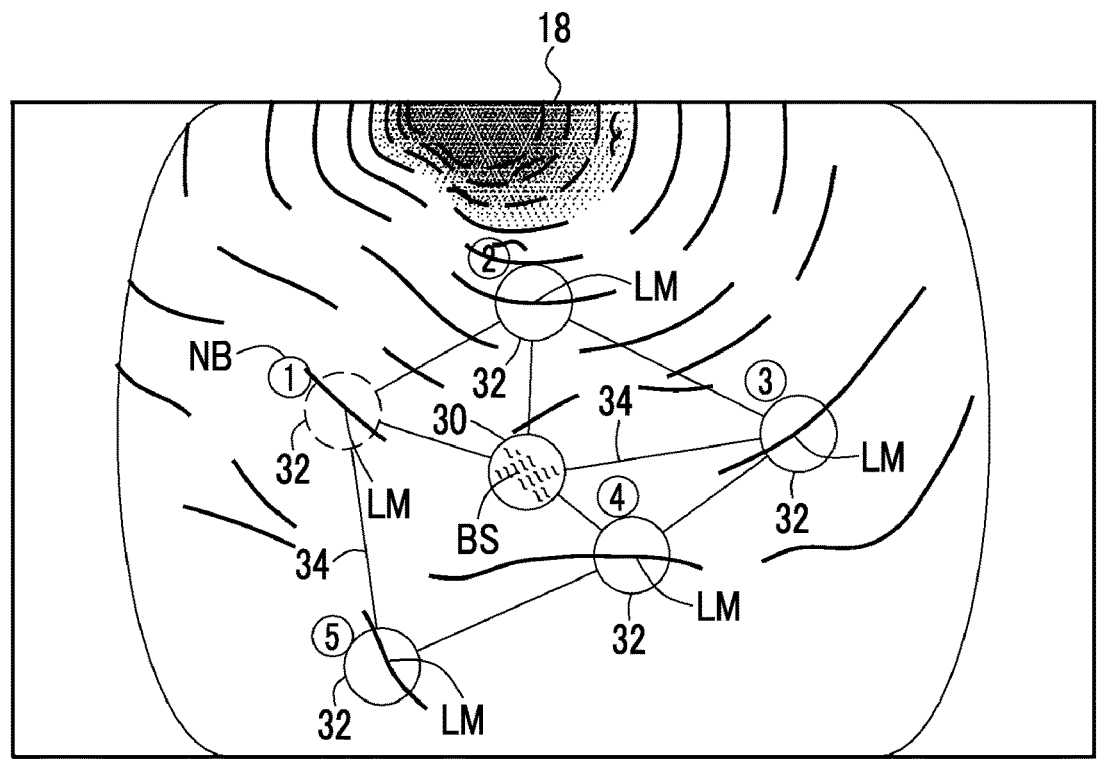
FIG. 7 is an image diagram showing a display mode of a landmark position display circle of a landmark with low reliability degree related to detection.

A processing unit for performing the landmark detection process in the landmark processing unit 22 is preferably a trained model for landmark detection that has been trained through machine learning using teacher image data including the landmarks. In a case where the landmark processing unit 22 can calculate the reliability degree related to the detection of the landmark, it is preferable to change a display mode (color, line style, or the like) of the position information of the landmark according to the reliability degree. For example, as shown in FIG. 7, in a case where the reliability degree of the landmark LM having the distinction number "1" is lower than the reliability degrees of the other landmarks LM, it is preferable to make a display mode (dotted line in FIG. 7) of the landmark position display circle 32 of the landmark LM having the distinction number "1" different from display modes (solid lines in FIG. 7) of the landmark position display circles 32 of the other landmarks LM.

The display control unit 23 performs any of an actual position display control process of displaying the actual position information of the detection target on the display 18 in a case where the detection target is detected, or a landmark display control process of displaying the position information of the landmark on the display 18 in a case where the detection target is not detected. As shown in FIG. 8, by the actual position display control process, in the endoscope image of the display 18, the detected position display circle 30 is displayed as the actual position information of the detection target, and the landmark position display circle 32 is displayed as the position information of the landmark LM. It is preferable that the link line 34 is also displayed on the display 18 in the actual position display control process. In FIG. 8, the position information of the landmark is displayed together in the actual position display control process, but the position information of the landmark need not be displayed.

Then, in a case where the display of the detection target disappears from the endoscope image due to a case where a large amount of blood (blood pool BP) flows out from the bleeding portion, the detection target is not detected by the detection target detection unit 21. Even in a case where the display of the detection target disappears as described above, the detection of the landmark is maintained by the landmark processing unit 22 in a case where the landmark remains in the endoscope image. In this case, by performing the landmark display control process, the landmark position display circle 32 is displayed on the display 18 as the position information of the landmark even though the detected position display circle 30 is not displayed. It is preferable that the link line 34 is also displayed on the display 18 in the landmark display control process.

Further, the display control unit 23 may perform any of an actual position display control process of displaying the actual position information of the detection target on the display 18 in an actual position display mode in a case where the detection target is detected, or an estimated position display control process of displaying the estimated position information of the detection target on the display 18 in an estimated position display mode different from the actual position display mode in a case where the detection target is not detected. By making the actual position display mode and the estimated position display mode different from each other in this manner, the user can determine an actual position or an estimated position, and can recognize that a target displayed at the actual position is an estimated target. On the other hand, in a case where only the estimated position display is performed without the actual position display, there is no timing at which the user recognizes whether or not the estimated target is the detection target. In this case, in a case where the estimated target is a target different from the detection target desired to be detected by the user, the estimated target is erroneously recognized as the detection target. The estimated position information of the detection target is calculated by the estimated position information calculation unit 24.

In a case where the detection target is not detected, the estimated position information calculation unit 24 calculates estimated position information of the detection target by a position information estimation process based on the endoscope image. As shown in FIG. 9, in a case where the display of the detection target disappears due to the outflow of the blood pool BP, the estimated position information calculation unit 24 calculates the estimated position information of the detection target by performing the position information estimation process. Then, the display control unit 23 performs the estimated position display control process to display, as the estimated position information of the detection target, an estimated position display circle 36 in a portion where the detection target is estimated to be located. Accordingly, in a case where the detection target is the bleeding portion BS, the time required for hemostasis can be shortened.

It is preferable that, in the position information estimation process, the estimated position information is calculated from a detection target region including the detection target in order to suppress the erroneous detection. Specifically, the blood pool BP is specified as a detection target region, and the estimated position information is calculated from the region of the blood pool BP. It is preferable to use a feature amount (a color feature amount corresponding to the blood pool BP, or the like) of the endoscope image in order to specify the blood pool BP.

It is preferable that the estimated position information of the detection target is calculated from a positional relationship between the landmark position display circles 32, for example, a shape of a link formed from the link line 34 in the position information estimation process. In addition, it is preferable that the estimated position information of the detection target is calculated from a difference in pixel value between the endoscope images obtained at different timings in the position information estimation process. In addition, it is preferable that the estimated position information of the detection target is calculated from an optical flow of a blood flow near the detection target from the endoscope image in the position information estimation process. In addition, it is preferable that the estimated position information of the detection target is calculated from a density of blood in the endoscope image in the position information estimation process. In addition, it is preferable that the estimated position information of the detection target is calculated from oxygen saturation calculated from the endoscope image in the position information estimation process. In addition, it is preferable that the estimated position information of the detection target is calculated using a trained model for landmark detection that has been trained through machine learning using teacher image data for obtaining the estimated position information of the detection target in the position information estimation process.

It is preferable that the actual position display mode in which the actual position information of the detection target is displayed on the display 18 and the estimated position display mode in which the estimated position information of the detection target is displayed on the display 18 are different from each other in order to easily distinguish between the actual position and the estimated position of the detection target. Accordingly, since the user can recognize the estimation of the estimated position information of the detection target, it is possible to grasp that there is a probability that the information is incorrect.

Specifically, it is preferable that in a case where position display color information is used for displaying the actual position information and the estimated position information of the detection target, the position display color information of the actual position display mode is different from the position display color information of the estimated position display mode. For example, as shown in FIG. 10, the position display color information of the actual position display mode is set to "blue", and the position display color information of the estimated position display mode is set to "green", whereby the user easily distinguishes between the actual position information and the estimated position information.

Further, it is preferable that in a case where a position display figure is used for displaying the actual position information and the estimated position information of the detection target, the position display figure of the actual position display mode is different from the position display figure of the estimated position display mode. Specifically, it is preferable that in a case where the position display figure is a circle or an ellipse, an actual position line type is different from an estimated position line type. For example, in FIG. 9, the actual position line type of the detected position display circle 30 is represented by a single circle, whereas the estimated position line type of the estimated position display circle 36 is represented by a double circle.

Further, it is preferable that in a case where the position display figure is a circle or an ellipse, an actual position line thickness is different from an estimated position line thickness. For example, it is preferable that the detected position display circle 30 is represented by a circle of which the actual position line thickness is a thin line, and the estimated position display circle 36 is represented by a circle of which the estimated position line thickness is a thick line. Further, it is preferable that in a case where the position display figure is a circle or an ellipse, an actual position size is different from an estimated position size. For example, it is preferable that the detected position display circle 30 is represented by a circle of which the actual position size is small in diameter, and the estimated position display circle 36 is represented by a circle of which the estimated position size is large in diameter.

Further, a shape of the position display figure of the actual position display mode may be different from a shape of the position display figure of the estimated position display mode. For example, it is preferable that the position display figure of the actual position display mode is a circle or an ellipse, and that the position display figure of the estimated position display mode is a polygon (rectangle or the like). On the other hand, it is preferable that the position display figure of the actual position display mode is a polygon (rectangle), and that the position display figure of the estimated position display mode is a circle or an ellipse.

In a case where the display 18 has a main screen 18a on which the endoscope image is displayed and a sub screen 18b provided at a position different from a position of the main screen 18a, the detected position display circle 30, which is the actual position information of the detection target, may be displayed on the main screen 18a as the actual position display mode as shown in (A) of FIG. 11, and the estimated position display circle 36, which is the estimated position information of the detection target, may be displayed on the sub screen 18b as the estimated position display mode as shown in (B) of FIG. 11. On the sub screen 18b, the estimated position display circle 36 is superimposed and displayed on the same real-time endoscope image as on the main screen 18a. In FIG. 11, the landmark position display circle 32 is displayed on the main screen 18a in the actual position display mode, but may not be displayed. In addition, in the estimated position display mode, the landmark position display circle 32 is displayed on both the main screen 18a and the sub screen 18b, but at least one of the landmark position display circle 32 on the main screen 18a or the landmark position display circle 32 on the sub screen 18b may not be displayed.

Further, in a case where the display 18 has a main screen 18a on which the endoscope image is displayed and a sub screen 18b provided at a position different from a position of the main screen 18a, as shown in FIG. 12, the estimated position display circle 36, which is the estimated position information of the detection target, may be displayed on the main screen 18a in the estimated position display mode, and the detected position display circle 30, which is the actual position information of the detection target, may be displayed on the sub screen 18b in the actual position display mode by the estimated position display control process. In this case, it is preferable to superimpose and display the detected position display circle 30 on the still image of the endoscope image obtained at a timing at which the detection target is detected on the sub screen 18b. In FIG. 12, the landmark position display circle 32 is displayed on both the main screen 18a and the sub screen 18b, but at least one of the landmark position display circle 32 on the main screen 18a or the landmark position display circle 32 on the sub screen 18b may not be displayed.

In a case where the still image of the endoscope image is displayed on the sub screen 18b, depending on the position of the distal end part 12d of the endoscope, the position in vertical and horizontal directions of the real-time endoscope image on the main screen 18a may be different from the position in vertical and horizontal directions of the still image of the endoscope image on the sub screen 18b. For example, as shown in (A) of FIG. 13, the real-time endoscope image of the main screen 18a and the still image of the endoscope image of the sub screen 18b may be vertically reversed. In this case, a rotation state detection unit (not shown) provided in the extended processor device 17 detects a rotation state from the real-time endoscope image of the main screen 18a. Then, as shown in (B) of FIG. 13, an image rotation unit (not shown) provided in the extended processor device 17 rotates the still image of the endoscope image of the sub screen 18b such that the still image of the endoscope image of the sub screen 18b matches the real-time endoscope image of the main screen 18a in the vertical direction on the basis of the detected rotation state.

It is preferable that in the estimated position display control process, the estimated position display mode is changed according to a reliability degree of the estimated position information. In this case, the estimated position information calculation unit 24 calculates the reliability degree of the estimated position information in accordance with the calculation of the estimated position information. For example, it is preferable to calculate a confidence degree for the estimated position information as the reliability degree for the estimated position information from a model that has been trained through machine learning. The user can select an operation on the observation target according to the reliability degree of the estimated position information. For example, in a case where the reliability degree is high, a hemostasis process for the bleeding portion BS is performed, whereas in a case where the reliability degree is low, the hemostasis process is not performed in order to avoid hemostasis at a wrong portion.

Specifically, as shown in FIG. 14, in a case where the estimated position information is represented by the position display color information, the density of the position display color information is increased in a case where the reliability degree of the estimated position information is high reliability equal to or higher than a predetermined value, and the density of the position display color information is decreased in a case where the reliability degree of the estimated position information is low reliability less than the predetermined value. Further, in a case where the estimated position information is represented by the position display figure, the size of the position display figure is reduced in the case of high reliability degree, and the size of the position display figure is increased in the case of low reliability degree. Since a range in which the detection target exists can be limited in the case of high reliability degree, the size of the position display figure can be reduced. On the other hand, in the case of low reliability degree, the size of the position display figure is increased in order to display the range in which the detection target may exist as much as possible.

In the case of high reliability degree, the line thickness of the position display figure is increased, and in the case of low reliability degree, the line thickness of the position display figure is reduced. Further, in the case of high reliability degree, the line type of the position display figure is set to a solid line, and in the case of low reliability degree, the line type of the position display figure is set to a dotted line. As described above, the reliability degree of the estimated position information can be intuitively grasped by changing the estimated position display mode according to the reliability degree.

It is preferable that the processing timing setting unit 27 sets a start timing or an end timing of the detection target detection process and a start timing or an end timing of the position information estimation process (see FIG. 4). By setting the start timing and the end timing in this way so that the detection target detection process or the position information estimation process is not always performed, it is possible to suppress the erroneous detection. In addition, in a case where it is determined that the detection target detection process or the position information estimation process is not necessary, the actual position information and the estimated position information of the detection target are not displayed, and thus it is possible to make it easy to see a part other than the detection target such as a bleeding point.

Specifically, as shown in FIG. 15, it is preferable that the start timing of the detection target detection process is a timing at which water supply sent from the distal end part of the endoscope 12 to the observation target is detected in the endoscope image (at the time of water supply detection), a timing at which incision made in a part of the observation target by a treatment tool or the like is detected in the endoscope image (at the time of incision detection), or a timing at which the treatment tool protruding from the distal end part of the endoscope 12 is detected in the endoscope image (at the time of treatment tool use detection).

In addition, it is preferable that the end timing of the detection target detection process is not only a timing at which the detection target cannot be detected (at the time of failure of the detection target detection process) but also a timing after a predetermined time has elapsed from the timing at which the detection target cannot be detected (after an elapse of a predetermined time after failure). The start timing of the position information estimation process is, for example, after the detection target detection process fails. In addition, it is preferable that the end timing of the position information estimation process is a timing at which the estimated position information cannot be calculated by the position information estimation process (at the time of failure of the position information estimation process). For example, at the time of the failure of the position information estimation process, information such as a landmark necessary for calculating the estimated position information may not be acquired.

In the tracking mode, as shown in FIG. 16, it is preferable that the detection target and the landmark are detected from the second endoscope image based on the second illumination light to perform the landmark setting process, and then the second illumination light is switched to the first illumination light, and the estimated position information of the detection target and the position information of the landmark are displayed on the first endoscope image based on the first illumination light. Accordingly, the position or the region of the detection target is not missed in a case where the second illumination light is switched to the first illumination light. It is preferable that the second illumination light is light suitable for detecting the detection target and the landmark, for example, special light including violet light capable of highlighting a structure. On the other hand, it is preferable that the first illumination light is light suitable for displaying the estimated position information of the detection target and the position information of the landmark, for example, white light.

Next, a series of flows in the tracking mode will be described with reference to a flowchart of FIG. 17. The tracking mode is turned ON by operating the mode selector switch 12 *f*. Then, in a case where the start timing of the detection target detection process set by the processing timing setting unit 27 is satisfied, the detection target detection process is performed on the endoscope image. In a case where the detection target including the bleeding portion BS is detected in the detection target detection process, the actual position information of the detection target is acquired. The actual position information of the detection target is displayed on the display 18 in the actual position display mode. In a case where the detection target is detected, the position information of the landmark may also be displayed on the display 18.

On the other hand, in a case where the detection target is not detected, the estimated position information of the detection target is calculated. It is preferable that the estimated position information is calculated based on the position information of the landmark. In a case where the estimated position information is calculated, the estimated position information of the detection target is displayed on the display 18 in the estimated position display mode. The estimated position display mode is different from the actual position display mode. For example, while the actual position information of the detection target is represented by a single circle, the estimated position information of the detection target is represented by a double circle, so that the actual position information and the estimated position information are easily distinguished from each other. The series of processes described above is repeatedly performed as long as the tracking mode is ON. Then, in a case where the mode selector switch 12 *f* is operated and the tracking mode is turned OFF, the detection of the detection target and the like are ended.

Since the endoscope 12 is manually operated, even though the estimated position of the detection target is continuously captured in the endoscope image, a range of the endoscope image may change, and in a case where the landmark LM surrounding the estimated position of the detection target does not fall within the endoscope image, the organ may be deformed and the relationship between the landmark and the detection target may be changed. As shown in FIG. 18, new landmarks LM2 may be detected at positions different from the positions of the landmarks LM used for the position information estimation process in a case where the endoscope 12 images the next frame, the landmarks LM used for the position information estimation process may be updated, and the display of the estimated position display circle 36 on the bleeding region BP may be continued.

In a case where the landmark LM used in the position information estimation process is updated, the landmark LM before update is set as the landmark LM and the landmark LM after update is set as the new landmark LM2. (A) of FIG. 18 a displays the estimated position display circle 36 in the position information estimation process by the landmark LM. In a case where a new frame is acquired, as shown in (B) of FIG. 18, a new landmark LM2 surrounding the estimated position of the detection target is detected in accordance with a moving direction of the preceding and following frame imaging, and a new landmark position display indicator 38 is displayed. Further, a new landmark setting process of associating the new landmark LM2 with the detection target estimated position information is performed to calculate a new relative relationship. The new relative relationship is displayed by a new link line 39. It is preferable that a dotted line or the like is used as the new link line 39, which is less conspicuous than the link line 34 and is not confusing. A number NB (distinction number) for distinguishing the respective landmark position display circles 32 can also be assigned to the new landmark position display indicator 38, but may not be assigned in a case where the visibility deteriorates. Further, the new landmark position display indicator 38 may have the same shape as or a different shape from the landmark position display circle 32.

After the new landmark setting process, in a case where the endoscope 12 acquires an endoscope image of a new frame and the landmark LM necessary for the position information estimation process is not recognized, as shown in (C) of FIG. 18, a new position information estimation process based on the new relative relationship is performed, the detection target estimated position information is calculated, and the estimated position display circle 36 is displayed on the display 18. Since the position information estimation process by the landmark LM is ended, the link line 34 is not displayed, and the new link line 39 is displayed by a solid line such as the link line 34. For the landmark LM that continues to be detected, the landmark position display circle 32 may be displayed immediately after the update of the position information estimation process, but it is preferable that the landmark position display indicator 32 is not displayed after an elapse of a predetermined time.

Since the range imaged by the endoscope 12 moves even from the state of the position information estimation process using the new landmark LM2, the update of the landmark LM used for the position information estimation process continues. With the new landmark LM2 as the landmark LM and the new link line 39 as the link line 34, the new landmark LM2 updates the relative relationship by the new landmark setting process, and the landmark LM performs the position information estimation process.

In the above-described embodiment, hardware structures of processing units executing various processes, such as the image acquisition unit 20, the detection target detection unit 21, the landmark processing unit 22, the display control unit 23, the estimated position information calculation unit 24, the detection memory 26, or the processing timing setting unit 27 are various processors as follows. The various processors include a central processing unit (CPU) that is a general-purpose processor that executes software (programs) to function as various processing units, a graphical processing unit (GPU), a programmable logic device (PLD) that is a processor capable of changing a circuit configuration after manufacture, such as a field programmable gate array (FPGA), and an exclusive electric circuit that is a processor having a circuit configuration exclusively designed to execute various kinds of processing.

One processing unit may be configured of one of these various processors, or may be configured of a combination of two or more processors of the same type or different types (for example, a plurality of FPGAs, a combination of a CPU and an FPGA, or a combination of a CPU and a GPU). In addition, a plurality of processing units may be constituted by one processor. As an example in which the plurality of processing units are configured of one processor, first, as typified by computers such as a client or a server, one processor is configured of a combination of one or more CPUs and software, and this processor functions as the plurality of processing units. Second, as typified by a system on chip (SoC) or the like, a processor that implements the functions of the entire system including the plurality of processing units by using one integrated circuit (IC) chip is used. As described above, the various processing units are configured using one or more of the various processors as a hardware structure.

Further, the hardware structure of these various processors is more specifically an electric circuit (circuitry) in a form in which circuit elements such as semiconductor elements are combined. The hardware structure of the storage unit is a storage device such as a hard disc drive (HDD) or a solid state drive (SSD).

EXPLANATION OF REFERENCES

10: endoscope system
12: endoscope
12a: insertion part
12b: operating part
12c: bendable part
12d: distal end part
12f: mode selector switch
12g: still image acquisition instruction switch
12h: zoom operation part
13: light source device
14: processor device
15: display
16: user interface
17: extended processor device
18: display
18a: main screen
18b: sub screen
20: image acquisition unit
21: detection target detection unit
22: landmark processing unit
23: display control unit
24: estimated position information calculation unit
26: detection memory
27: processing timing setting unit
30: detected position display circle
32: landmark position display circle
34: link line
36: estimated position display circle
38: new landmark position display indicator
39: new link line
BP: blood pool
L: illumination light
L1: first illumination light
L2: second illumination light
BS: bleeding portion
LM: landmark
LM2: new landmark

What is claimed is:

1. An endoscope system comprising:
one or more processors configured to:
    acquire an endoscope image;
    detect a detection target and acquire actual position information of the detection target by performing a detection target detection process on the endoscope image;
    calculate estimated position information of the detection target by a position information estimation process based on the endoscope image in a case where the detection target is not detected; and
    perform the following:
        an actual position display control process of displaying the actual position information of the detection target on a display in an actual position display mode, in a case where the detection target is detected, and an estimated position display control process of displaying the estimated position information of the detection target in a portion where the detection target is estimated to be located on the display in an estimated position display mode different from the actual position display mode, in a case where the detection target is not detected,
    wherein, in the estimated position display control process, the estimated position display mode is changed according to a reliability degree of the estimated position information, and
    wherein, in the estimated position display control process, the one or more processors calculate the reliability degree of the estimated position information by using a trained machine learning model, and the estimated position information is displayed on the display in different display modes according to the calculated reliability.

2. The endoscope system according to claim 1,
wherein, in a case where position display color information is used for displaying the actual position information and the estimated position information of the detection target, the position display color information of the actual position display mode is different from the position display color information of the estimated position display mode, or
in a case where a position display figure is used for displaying the actual position information and the estimated position information of the detection target, the position display figure of the actual position display mode is different from the position display figure of the estimated position display mode.

3. The endoscope system according to claim 2,
wherein, in a case where the position display figure is a circle or an ellipse, at least any of a case where an actual position line type and an estimated position line type are different from each other, a case where an actual position line thickness and an estimated position line thickness are different from each other, or a case where an actual position size and an estimated position size are different from each other is true.

4. The endoscope system according to claim 2,
wherein a shape of the position display figure of the actual position display mode is different from a shape of the position display figure of the estimated position display mode.

5. The endoscope system according to claim 1,
wherein, in a case where the display has a main screen on which the endoscope image is displayed and a sub screen provided at a position different from a position of the main screen, the estimated position information of the detection target is displayed on the sub screen as the estimated position display mode.

6. The endoscope system according to claim 1,
wherein, in a case where the display has a main screen on which the endoscope image is displayed and a sub screen provided at a position different from a position of the main screen, the estimated position information of the detection target is displayed on the main screen in the estimated position display mode and the actual position information of the detection target is displayed on the sub screen in the actual position display mode by the estimated position display control process.

7. The endoscope system according to claim 1,
wherein, in the position information estimation process, the estimated position information is calculated from a detection target region including the detection target.

8. The endoscope system according to claim 1,
wherein the one or more processors are configured to set at least any of a start timing or an end timing of the detection target detection process, or a start timing or an end timing of the position information estimation process.

9. The endoscope system according to claim 1,
wherein the detection target is at least any of a bleeding portion, a lesion part, a shape of a specific organ, a mucous membrane pattern, marking after cauterization, or marking given to a body.

10. An endoscope system comprising:
one or more processors configured to:
    acquire an endoscope image;
    acquire detection target actual position information of a detection target by performing a first detection process on the endoscope image;
    acquire position information of a landmark by performing a second detection process on the endoscope image; and
    perform a landmark setting process of setting a relative relationship by associating the detection target actual position information and detection target estimated position information obtained from a position information estimation process based on the position information of the landmark, with the position information of the landmark, each time the endoscope image is updated and the detection target actual position information and the detection target estimated position information is acquired,
    wherein, in the position information estimation process, an estimated position display mode is changed according to a reliability degree of the estimated position information, and
    wherein, in the position information estimation process, the one or more processors calculate the reliability degree of the estimated position information by using a trained machine learning model, and the estimated position information is displayed on a display in different display modes according to the calculated reliability.

11. The endoscope system according to claim 10,
wherein, in a case where a new landmark is detected by acquiring the endoscope image of a new frame in a state where the position information estimation process is continued, a new landmark setting process of setting a new relative relationship by associating the detection target estimated position information with the new landmark is performed as the landmark setting process, after the new landmark setting process, in a case where the landmark necessary for the position information estimation process is not recognized, a position information estimation process based on the new relative relationship is performed, and a new detection target estimated position information is calculated, and
the new detection target estimated position information is displayed on the display.

12. The endoscope system according to claim 11,
wherein the new landmark is position information of at least any of a mucous membrane pattern, a shape of an organ, or marking by a user operation.

13. A method of operating an endoscope system, the method comprising:
following steps, executed by one or more processors, of:
    acquiring an endoscope image;
    detecting a detection target and acquiring actual position information of the detection target by performing a detection target detection process on the endoscope image;
    calculating estimated position information of the detection target by a position information estimation process based on the endoscope image in a case where the detection target is not detected; and
    performing the following:
        an actual position display control process of displaying the actual position information of the detection target on a display in an actual position display mode in a case where the detection target is detected, and
        an estimated position display control process of displaying the estimated position information of the detection target in a portion where the detection target is estimated to be located on the display in an estimated position display mode different from the actual position display mode in a case where the detection target is not detected,
        wherein, in the estimated position display control process, the estimated position display mode is changed according to a reliability degree of the estimated position information, and
        wherein, in the estimated position display control process, the one or more processors calculate the reliability degree of the estimated position information by using a trained machine learning model, and the estimated position information is displayed on the display in different display modes according to the calculated reliability.

* * * * *